United States Patent [19]

Smith

[11] 4,439,423

[45] Mar. 27, 1984

[54] CHYMOPAPAIN AND METHOD FOR ITS USE

[75] Inventor: William S. Smith, Libertyville, Ill.

[73] Assignee: Smith Laboratories, Inc., Rosemont, Ill.

[21] Appl. No.: 263,197

[22] Filed: May 13, 1981

[51] Int. Cl.$^3$ .............................................. A61K 37/48
[52] U.S. Cl. ...................................................... 424/94
[58] Field of Search ................... 424/94; 435/212, 219

[56] References Cited

U.S. PATENT DOCUMENTS

| | | | |
|---|---|---|---|
| 2,313,875 | 12/1980 | Jansen et al. | 195/66 |
| 3,248,300 | 4/1966 | Burdick | 195/2 |
| 3,274,072 | 9/1966 | Burdick | 195/2 |
| 3,281,331 | 10/1966 | Bergkvist | 195/66 |
| 3,284,316 | 11/1966 | Cayle | 195/63 |
| 3,320,131 | 5/1967 | Smith | 167/73 |
| 3,558,433 | 1/1971 | Stern | 195/66 |
| 4,039,682 | 8/1977 | Ausman et al. | 424/319 |

FOREIGN PATENT DOCUMENTS

| | | |
|---|---|---|
| 7322964 | 1/1978 | France . |
| 1512491 | 6/1978 | United Kingdom . |

OTHER PUBLICATIONS

Ebata et al.,—The J. of Biological Chemistry, vol. 237, No. 4, Apr. 1962, pp. 1086-1094.
Skelton—Chem. Abst., vol. 70, (1969), p. 34597k.
Summers et al., Genetics, vol. 60, Aug. 1971, pp. 603-607.
GRAS Substances—Sulfiting Agents 47 F.R. 29956, Jul. 1982.
Sussmuth et al., *Mutagen Res.*, vol. 40, 229-236, (1976).
Erlanger, *Arch. Biochem. Biophys.* 95, 271-278, (1961).
Baines et al., *J. Biochem* 177, 541-548, (1979).

Jansen and Balls, *J. Bio. Chem.*, vol. 137 459, (1941).
The Merck Index, Ninth Edition, Entry No. 2261, p. 293.
Cayle and Lopez—Ramos, Abstracts of Papers of the 140th Meeting of the Am. Chem. Soc'y., Chicago, p. 19C, (1961).

F. Mukai et al., *Biochim. Biophys. Res. Comm.* 39, 983-988, (1970).
Shapiro, *Mutagen Res.*, vol. 39, 149-176, (1977).
McCluskey and Thomas, The Removal of Cartilage Matrix, In Vivo, by Papain, 108 *J. Exp. Med.* 371, (1958).
Potter et al., The Removal of Cartilage Matrix by Papain, 112 *J. Exp. Med.* 1173, (1960).
Hirsch, Studies on the Patholoy of Low Back Pain, 41B *J. Bone Jt. Surg.*, 237, (1959).
Mitchell et al., The Chemical Background of Intervertebral Disc Prolapse, 43B *J. Bone Jt. Surg.*, 141, (1961).
Harris and McNab, Structural Changes in the Lumbar Intervertebral Discs, 36B *J. Bone Jt. Surg.*, 304, (1954).
Feffer, Treatment of Low-Back and Sciatic Pain by the Injection of Hydrocortisone into Degenerated Intervertebral Discs, 38A *J. Bone Jt. Surg.*, 585, (1956).
Davidson et al., Biochemical Alterations in Herniated Disks, 234 *J. Bio. Chem.* 2951, (1959).
Smith et al., Enzyme Dissolution of the Nucleus Pulposus in Humans, *Nature*, vol. 198, 1311, (1963).
Kunimitsu and Yasunobu, *Biochim. Biophys. Acta*, vol. 139, pp. 405-417, (1967).

*Primary Examiner*—Sam Rosen
*Attorney, Agent, or Firm*—Neuman, Williams, Anderson & Olson

[57] ABSTRACT

An improved method for treating an intervertebral spinal disc in a mammalian subject which disc exhibits an abnormal condition, characterized by a reduced risk of toxic effect to the subject is provided which comprises, injecting in said disc an amount of a pharmaceutically acceptable solution of a purified chymopapain essentially free of proteolytically inactive and/or toxic protein components, said purified chymopapain being used in an amount sufficient to selectively dissolve the nucleus pulposus of said disc.

Pharmaceutical compositions are also provided for said method which include a purified proteolytically active lyophilized chymopapain, essentially free of proteolytically inactive and toxic components, and an activating amount of a pharmaceutically acceptable reducing agent.

17 Claims, 1 Drawing Figure

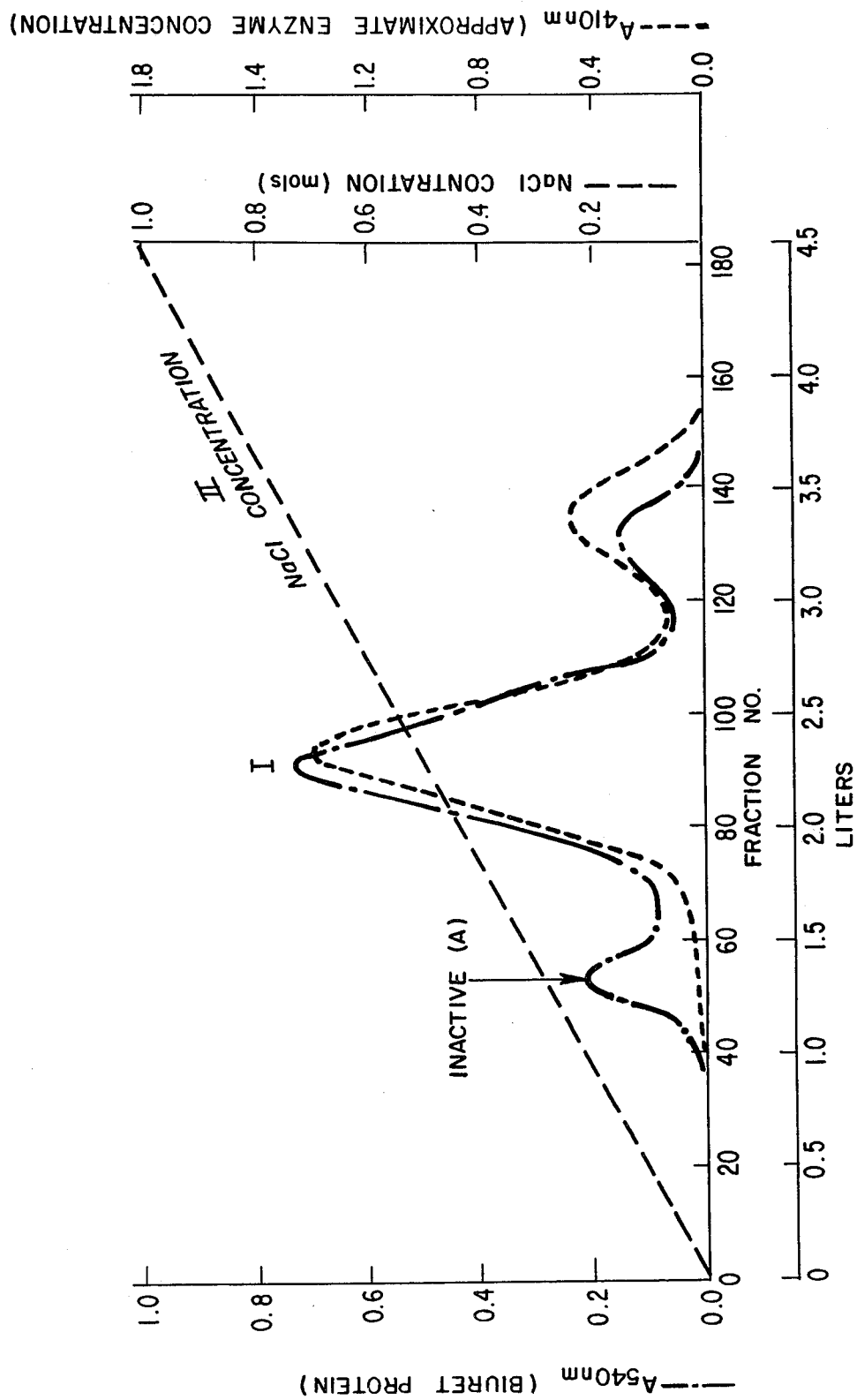

CHYMOPAPAIN AND METHOD FOR ITS USE

FIELD OF THE INVENTION

This invention relates to an improved chymopapain, improved formulations of chymopapain, and methods for the treatment of abnormal intervertebral discs using purified chymopapain.

DESCRIPTION OF THE PRIOR ART

Chymopapain is an enzyme which is the major proteolytic component of the crude latex of *Carica papaya,* caricaceae. It is characterized as a sulfhydryl enzyme similar to papain, but differs in respect to substrate specificities, electrophoretic mobility, stability, and solubility. It was first characterized and described by Jansen and Balls, J. Biol. Chem., vol. 137, pp. 459-60 (1941) and in U.S. Pat. No. 2,313,875 (1943). See The Merck Index, Ninth Edition, Entry No. 2261, p. 293.

The Jansen and Balls method for the preparation of chymopapain is essentially a salting-out procedure which consists of acidifying a solution of the soluble portion of the latex of papaya to a pH of about 2, separating the insoluble protein fraction from the liquid phase, raising the pH to 4, removing more protein, saturating the retained liquid phase with sodium chloride, and then reducing the pH to about 2 to precipitate chymopapain.

Other researchers in the field have reported that the Jansen and Balls procedure when applied to a commercial papaya latex does not produce a single crystalline protein as described herein. See for example, Cayle and Lopez-Ramos, Abstracts of Papers of the 140th Meeting of the Am. Chem. Soc'y, Chicago, p. 19C (1961); Ebata and Yasunobu, J. Biol. Chem., vol. 237, pp. 1086-94 (1962); Kunimitsu and Yasunobu, Biochim. Biophys. Acta, vol. 139, pp. 405-17 (1967). Chymopapain separated from papaya by salt fractionation, and/or solvent fractionation, and/or pH adjustment or by the use of similar methods is hereinafter referred to as crude chymopapain. Crude chymopapain has a distinct "sulfurous" odor as well as a pronounced yellow-brown color in solution.

Crude chymopapain in fact contains a variety of materials of a proteinaceous nature, of which only two are consistently active proteolytic factors. For example, in Stern, U.S. Pat. No. 3,558,433, patented Jan. 26, 1971, a method is described for identifying the components of crude chymopapain containing three components, namely two active proteolytic fractions known as chymopapain I and II and a proteolytically inactive proteinaceous component.

The procedure of U.S. Pat. No. 3,558,433 specified the use of a chromatographic column of carboxymethyl substituted cross-linked dextran copolymer exchange resin previously equilibrated with an aqueous buffer solution at a pH of about 8 to about 8.5 to which the crude chymopapain was applied and then eluted by passing an aqueous buffer of the solution through an exchanger having the same pH, but a greater ionic strength than the buffer solution used for equilibrating of the chromatographic column in the first instance. The chymopapain product obtained by that procedure while purer than the crude chymopapain of Jansen and Balls was never used in the treatment of herniated intervertebral discs as described in U.S. Pat. No. 3,320,131.

The Stern Patent, U.S. Pat. No. 3,558,433 teaches that the purified chymopapain produced by the method described therein behaves essentially like a single protein by virtue of formation of a single symmetrical boundary in the analytical ultracentrifuge and by the formation of a single precipitation zone in an immunodiffusion test run in an agar gel diffusion system.

More recently it has been found that the first fraction of chymopapain eluted from the chromatographic column by the Stern patent procedure and there described as proteolytically "inactive", is in the case of some papaya extracts prepared by newer methods [Barnes et al, Biochem. J. 177, 541-48 (1979)], actually proteolytically active, depending on the source of the raw material.

While the Stern patent identifies various components of chymopapain by the absorption peak eluent maxima as shown in the drawings, the example of the patent shows that all of the fractions of the chymopapain eluent were combined, dialyzed against distilled water and lyophilized to make the purified chymopapain product.

It is noted that the chymopapain produced by the process of Jansen and Balls was widely used in clinical trials to reduce by chemonucleolysis, herniated discs in human patients following the procedure of Smith U.S. Pat. No. 3,320,131, i.e., the injection of a herniated spinal disc in an animal with the chymopapain in an amount sufficient to selectively dissolve the nucleus pulposus of said disc. These clinical trials, however, indicated the presence of significant and potentially life threatening allergic side reactions in about 0.5 percent of the patients. In addition, a small number of patients developed delayed allergic reactions which may have been as high as about three percent of the patients treated. The reasons for the high incidence of anaphylactic side reactions that were reported by the clinical investigators using the then available chymopapain prepared by the method of Jansen and Balls, to reduce and treat herniated discs was not specifically known, and was never fully elucidated or explained to this date.

The crude chymopapain of Jansen and Balls which was used in the previous clinical trials however contains an unnecessary anaphylactic risk liability by virtue of the presence of the first eluted fraction of chymopapain which is described as proteolytically inactive in the Stern patent, since it is well known that the injection of foreign protein antigens into mammals necessarily carries with it a risk of anaphylactic shock. The greater the variety of antigens, the more chance that the subject will be sensitive. However, the beneficial effects sought by these injections outweighs the necessary incidental risks under certain circumstances, such as with vaccines used in the treatment of rabies infection, or tetanus antitoxin prepared from animal souces.

Sound medical practice, however, dictates that the injection of a proteinaceous substance which contains a further or supernumerary protein component which may have potentially lethal toxic manifestations and the effectiveness of which additional component for the medical treatment is questionable, bears an unnecessary unacceptable risk of anaphylaxis for the patient undergoing such treatment.

Since, the injection of medically indicated foreign protein agents such as crude chymopapain into mammalian systems always include some risk, to obtain the maximum benefits of such procedure, it is desirable to have only the active proteinaceous enzyme components in as pure and as concentrated a form as possible for the indicated medical purposes as well as being essentially free of components which are suspected as sensitizing antigens to thereby minimize protein immunogenicity and consequent anaphylactic shock in the patient.

Additionally, the minimization of colored protein materials, and odoriferous substances present in the crude chymopapain reduces the risk of anaphylactic shock to patients because these characteristics are usually suspect in immunogenic reactions.

It has also been noted that the prior art describes the treatment of damaged or abnormal discs by controlled dissolution with crude chymopapain solutions which contain sodium bisulfite added as a preservative as described in U.S. Pat. No. 4,039,682 (1977).

However, such use of sodium bisulfite also carries with it an unacceptable risk of mutagenic activity. For example, F. Mukai et al. in *Biochim. Biophys. Res. Comm.* 39, 983–988 (1970) showed that some mutagenic activity was observed in the treatment of *E. Coli* with sodium bisulfite resulting in a significant increase in the number of reversions. Shapiro, Mutagen Research, vol. 39, 149–176 (1977), also indicated that bisulfite in low concentrations inhibited DNA synthesis, cell division and mitosis in addition to inducing chromosome aberrations and mutations. Likewise, Sussmuth et al. Mutagen Res. 40, 229–36 (1976) showed 4,500 mutants per million survivors (0.1%) of *E. Coli B.* treated with sodium bisulfite at a pH of 6. Accordingly, the benefits of bisulfite as a preservative would appear to carry with it unacceptable and unnecessary risks of precancerous modifications in patients to whom it is administered, particularly when evidence exists that pharmaceutical stability is not contingent upon the presence of bisulfite.

SUMMARY OF THE INVENTION

The present invention comprises purified chymopapain of lower immunogenicity and toxicity, prepared by an improved process, and more particularly, to a pharmaceutical composition consisting essentially of a purified chymopapain and a pharmaceutically acceptable, non-toxic reducing agent. The pharmaceutical composition is further characterized by freedom from sodium bisulfite and EDTA and excessive odor and color.

The chymopapain application of Stern, Ser. No. 263,196 filed on even date herewith (and incorporated herein by reference) describes a process for producing a purified chymopapain which comprises:

(a) contacting an aqueous buffered solution of crude chymopapain with a weakly acidic cationic exchanger comprising a column carboxymethyl substituted crosslinked agarose gel, said "cationic exchanger" having been previously equilibrated with aqueous buffer solution having a pH of between about 6.5 and 7.5 and having a neutralizing capacity of from 0.02 to 0.10 milliequivalents of sodium hydroxide per cc.

(b) eluting the chymopapain retained on the exchanger with an aqueous buffer solution having a pH in the same pH range as the buffer used for equilibrating the carboxymethyl substituted agarose gel, but having a linearly increasing ionic concentration of a compatible, non-reactive, water-soluble, pharmaceutically acceptable, neutral, inorganic salt with respect to eluent volume;

(c) collecting and discarding a first series of fractions of eluent from said exchanger containing an initially eluted colored and odoriferous protein component from crude chymopapain until the molarity of the eluent with respect to said soluble salt increases to and reaches the range of 0.25 to 0.4;

(d) continuously collecting and retaining a further series of fractions of chymopapain eluted from the exchanger comprising two proteolytically active chymopapain fractions at soluble salt concentrations greater than about 0.25 to 0.4 molar, until substantially all of the said absorbed chymopapain is recovered;

(e) recombining active fractions from step (d) and treating said retained fractions containing proteolytically active components of the chymopapain to remove the dissolved ionic inorganic salts and buffer components, and (f) lyophilizing the essentially salt-free purified chymopapain solution to produce a dry, purified chymopapain essentially free of proteolytically inactive components.

The purified chymopapain made by the above process is essentially free of inactive protein components, and is further characterized by its failure to form a precipitate in an acidified solution with barium chloride. This is in contrast with crude chymopapain which does form a precipitate under such conditions. While the reason why such precipitate forms with the unpurified chymopapain is not known, it has been determined that the formation of a precipitate is characteristic of both crude chymopapain and is also characteristic of the discarded portion of the chymopapain initially eluted from the exchanger in the purification process set forth above.

The present invention also relates to a dry, lyophilized pharmaceutical composition of improved stability comprising a purified chymopapain essentially free of odorous, highly colored, and free of proteolytically inactive or other component materials which form a precipitate with acidified barium chloride, and an activating amount of a pharmacologically acceptable reducing agent packaged in container or vials under vacuum conditions.

A preferred dosage unit form suitable for use in dissolving or treating the nucleus pulposus of an abnormal or damaged intervertebral disc by injection therein consists of about 10,000 to 11,500 proteolytic units of the purified chymopapain (nominally 10,000 units) produced by the process of the present invention and a sodium cysteinate hydrochloride activating agent packaged in an evacuated vial. The dosage unit form broadly consists of 15–30 (preferably 23) milligrams of purified chymopapain and 3.0 to 3.6 milligrams of a sodium cysteinate hydrochloride in an evacuated container. Preferably the reducing agent (cysteine) is present in an amount of about 15%—broadly from 10 to 20% by weight of the chymopapain.

The present invention further relates to a method of treating by chemonucleolysis a damaged, herniated or otherwise abnormal intervertebral mammalian spinal disc which method is characterized by a reduced risk of toxic effect on the subject mammal, which comprises the step of injecting into said disc a pharmaceutically acceptable aqueous solution of a purified chymopapain essentially free of proteolytically inactive materials, and which does not form a precipitate with barium chloride in an amount sufficient to selectively dissolve portions of said disc.

The present invention also relates to a method of treating an abnormal spinal disc in a mammalian subject which comprises the steps of:

(i) inserting a needle into said disc;

(ii) confirming the placement of said needle by means of x-ray; and (iii) injecting into said disc an amount of a pharmaceutically acceptable solution of a relatively non-toxic, purified chymopapain essentially free of inactive components to selectively dissolve the nucleus pulposus of said disc.

OBJECTS OF THE INVENTION

One of the objects of the present invention is the provision of a method for treating an abnormal intervertebral disc in a mammal by injecting said disc with a purified chymopapain which has a reduced risk of toxic and/or anaphylactic effect when introduced and injected into mammalian systems.

A still further object is the provision of a method of treating a herniated or otherwise abnormal spinal disc in a mammal which comprises the step of injecting into said disc an amount of a pharmaceutically acceptable solution of a concentrated essentially pure and fully active chymopapain fraction sufficient in amount to selectively dissolve the nucleus pulposus of said disc.

Another object is the provision of a method for inducing chemonucleolysis of an abnormal mammalian intervertebral disc by injection into said disc of purified chymopapain to selectively dissolve a portion of said disc.

Another object is the provision of a pharmacological composition of highly concentrated, essentially completely proteolytic purified chymopapain and a non-toxic pharmaceutically acceptable reducing agent which is suitable for injection into mammalian systems and which has a reduced toxic liability to the mammalian subject.

A further object is the provision of a dry, highly stable formulation of purified chymopapain and a reducing agent for said chymopapain in a dry lyophilized form.

A still further object is the provision of a purified chymopapain and a natural reducing agent in dry dosage unit form.

A still further object is the provision of a pharmaceutically acceptable composition of an essentially pure chymopapain which is essentially free of other non-proteolytically active protein or other components which composition is also relatively non-toxic to mammalian subjects.

DESCRIPTION OF THE PREFERRED EMBODIMENTS

The crude chymopapains used as the starting material for the production of the purified chymopapain used in the process of the present invention contains three chromotographically separable fractions or components of material that make up what is known as chymopapain. These components include a proteolytically inactive or active, colored, odorous component and two proteolytically active components herein called chymopapain I and II. The crude chymopapain is obtained by the method of Jansen and Balls, J. Biol. Chem., Vol. 13, pp. 459-60 (1941), which involves the treatment of a commercial papain concentrate by forming an aqueous acidic solution and saturating the solution with sodium chloride at a higher pH, decreasing the pH and thereafter dialyzing a solution of the crude chymopapain to produce a salt-free solution thereof, followed by lyophilizing of the solution to obtain a crude dry chymopapain product.

The crude chymopapain made by the method of Jansen and Balls as well as other crude chymopapains, may be purified to remove inactive, colored, odorless, and immunogenic components by the process of the co-pending application of Stern, Ser. No. 263,196 filed on even date herewith which is incorporated herein by reference. The following example illustrates that purification procedure using a crude chymopapain starting material prepared by the method of Jansen and Balls.

EXAMPLE 1

All steps are performed at refrigerator temperatures. (2°–8° C.).

A. Crude chymopapain (about 29 g) was dissolved in 190 ml of pH 7.4 sodium phosphate buffer to give a 5% W/V (weight/volume) solution of 2°–8° C.

B. The solution of crude chymopapain in buffer was added to a column of carboxymethyl substituted cross-linked agarose resin approximately 1.7 liters in volume (5×80 cm. approximate bed dimensions), which previously has been equilibrated with 0.05 M sodium phosphate buffer. The resin had a neutralizing capacity of about 0.05 milliequivalents of sodium hydroxide per cc.

C. A gradient of sodium chloride solution buffered with 0.05 M sodium phosphate to pH 7.4 was then applied to the inlet of the column, so that the sodium chloride concentration increased in a linear fashion from 0 to 1.0 M with volume. The gradient was so arranged that when about 4.6 liters had been admitted to the column the incoming sodium chloride concentration was one molar.

D. The column effluent was collected with the aid of a drop counter in fractions of 25 mls in test tubes over about 40 hours.

E. The protein content and activity of each fraction were analyzed. Total protein by the biuret test was performed on 0.5 ml samples taken from each fraction. Proteolytic activity was estimated by determining hydrolysis of DL-α-benzoyl-arginine-p-nitroanilide with 0.05 ml samples from the fractions by the method of Erlanger, Arch. Biochim. Biophys. 95, 271–78 (1961) adapted for use with chymopapain. A plot was made of the relative protein content against serially collected fractions. (See. FIG. 1 of the attached drawing)

F. The fractions containing the protein component which first eluted (along with deep brown colored components) from the column at sodium chloride concentrations of from zero to about 0.4 molar were discarded.

G. The remaining fractions recovered at concentration of from 0.4 to 1 molar were combined and dialyzed against several changes of distilled water at 2°–8° C. to remove sodium chloride and dissolved buffer.

H. The desalted product was then adjusted with 1 N NaOH to a pH of 6 and then lyophilized to yield approximately 16.3 grams of purified chymopapain.

Reference is made to the attached drawing which is a graphically illustrated plot of protein content of the serially collected fractions of eluent from the column (left hand vertical axis) against the volume (in milliliters) of eluent collected (horizontal axis). Also included in the same graph as a broken line is the NaCl or salt concentration (right hand vertical axis) in terms of NaCl molarity of from zero to 1 molar on a linear gradient, plotted against the eluent volume as shown. The protein content is conveniently measured by adding 0.5 ml of each fraction to 5 ml of biuret reagent, and determining the absorbance (A) at 540 nm ($A_{540}$) after 15 minutes. Proteolytic activity was plotted by absorption at 410 nm ($A_{410}$) of the complex made by a modification of the Erlanger method (supra) adapted to chymopapain.

The first chymopapain protein component was eluted from the column at sodium chloride molarities of from about zero to about 0.25 to 0.4 molar. It is characterized as a highly colored, odorous fraction and identified as peak A. This component was discarded. The protein identified as peak A (frequently proteolytically inactive), contains most of the color elements found in the crude chymopapain. This protein fraction "A" was also characterized as forming as precipitate with acidified barium chloride solution.

Subsequent fractions of eluent produced two additional and major peaks at sodium chloride concentrations of from 0.4 to 1 molar, which were identified as chymopapain I and II.

The chymopapain I and II components recovered from the column as shown in Example 1 above, are proteolytically active and did not form a precipitate with acidified barium chloride solution.

The crude chymopapain containing the proteolytically inactive protein component and the two proteolytically active components chymopapains I and II absorbed in the column is eluted from the column by a salt solution (i.e. NaCl) gradient in a buffer solution maintained at a pH of 6.5 to 7.5, preferably at a pH of from 7.3 to 7.5.

The initial component (Peak A) eluted from the column and discarded, constitutes about 15% by weight of the total material and is eluted at salt (NaCl) concentrations from zero up to about 0.25 to 0.4 molar. Depending on source, this component may be proteolytically active or inactive and usually contains most of the color and odor factors present in the crude chymopapain.

The remainder of the eluent comprises the proteolytically active chymopapain components I and II, which are recovered at salt concentrations from about 0.25 to 0.4 up to 1 molar. The two characteristic major peaks or protein constituents make up about 85% of the material collected, and are eluted at salt concentrations of about 0.5 and 0.8 molar as shown in the drawing.

The absorption and elution process described above is carried out at refrigerator temperatures of from about 2°-8° C. The eluent fractions collected containing chymopapain I and II are combined and dialyzed against water to remove salt, as well as soluble buffer components, and is then filtered and sterilized. The salt-free solution of essentially pure, proteolytically active chymopapain I and II is then lyophilized. The total yield is about 50-60% based on crude chymopapain starting material. Although some inactive material is removed, the activity per unit weight of the final product is not increased, probably because of enzyme (activity) lost during processing.

While the crude chymopapain heretofore used in the treatment of abnormal or herniated discs apparently has multiple fractions, the process of the present invention has removed a fraction of that protein (Peak A) which appears to be responsible for higher toxicity as observed in animal tests in which the crude and purified chymopapain of this invention are compared.

As noted herein, the purified chymopapain of the present invention may be distinguished from the crude chymopapain of the prior art by the barium chloride in acid solution (HCl) test. Formation of a precipitate with barium chloride is characteristic of the prior art crude (or toxic) chymopapain, whereas the purified chymopapain of the present invention does not form a precipitate.

The following example illustrates the barium chloride test procedure used to distinguish the crude and purified chymopapain materials:

EXAMPLE 2

A 10% (w/v) aqueous solution of each of the following chymopapain specimens was acidified with 1 ml of 1 N HCl to which was added 1 ml of 12% (w/v) barium chloride ($BaCl_2$) (prepared as a U.S.P. test solution (U.S. Pharmacopeia XX, p. 1103: 12 gm. of $BaCl_2$ to make 100 ml in distilled water). The following results were obtained:

|  | Result |
| --- | --- |
| Crude Chymopapain | |
| Run A | moderate to heavy precipitate |
| Run B | moderate precipitate |
| Run C | moderate precipitate |
| Run D | moderate to heavy precipitate |
| Purified Chymopapain | |
| Run E | clear |
| Run F | clear |
| Run G | essentially clear (slight haze) |
| Run H | clear |

The purified chymopapain of the present invention is also characterized by having a reduced color and odor as compared to the crude chymopapain starting material. The color and/or odor factors found in crude chymopapain are associated with the first (discard) component (A) of the chymopapain eluted from the chromatographic column which also forms a precipitate with barium chloride solution as noted above. This discarded precipitable component with its color and odor components found in the crude chymopapain is apparently associated with the observed toxicity (anaphylactic shock) of crude chymopapain to mammalian subjects when injected into their discs.

The reduced or minimal color of the instant purified chymopapain products, together with the failure of these purified products to form a precipitate with barium chloride solution under acid conditions, may be taken as a measure of their freedom from the components which carry with them a higher risk of toxicity and are believed to be responsible in large part for the anaphylactic or other toxic reactions and manifestations that have been found to occur in a number of subjects injected with the crude chymopapain used for this purpose.

The chymopapain produced by the present process may be used to treat diseased, abnormal or herniated discs in mammalian subjects, by direct injection with a needle into the disc of the subject of a solution of the purified chymopapain in sufficient quantity to dissolve the nucleus pulposus of the disc. It is usually preferred to employ a naturally occurring reducing agent with the chymopapain such as sodium cysteinate hydrochloride although other pharmacologically acceptable reducing agents such as gluthathione, sodium thioglycollate, cysteinyl glycine, dithioerythritol, dithiothreitol, or isomers (D, L, or DL) can be used. Sodium cysteinate hydrochloride is the most preferred activating or reducing agent.

While the prior art indicated that the chymopapain used for the treatment of intervertebral discs was preferably formulated with sodium bisulfite and EDTA as preservatives, the use of these materials was found not only to be potentially toxic but also not necessary. Actually, the use of sodium bisulfite is contraindicated because of its toxicity and in view of its mutagenic activity carrying with it the implied risk of carcinogenic activity.

A particular dosage unit form of the present purified chymopapain is contemplated which contains about 23 mg of the purified lyophilized chymopapain produced by the process of the present invention having about 10,000 to 11,500 units of enzyme activity and about 3.5 mg sodium of cysteinate hydrochloride packaged in an evacuated (vacuum) vial further characterized by the absence of sodium bisulfite or EDTA (ethylene diaminetetraacetic acid).

Generally, the cysteine or other reducing agent is used in amounts of from about 0.5 to 10 mg per 10,000 enzyme units of chymopapain determined by the Erlanger analysis.

The following is an example of the preparation of the lyophilized product of a typical dosage unit form dosage.

TYPICAL PREPARATION OF THE FORMULATION

1. Purified chymopapain as assayed by the method involving DL-α-benzoyl-p-nitroanilide hydrolysis, contained 522 units per mg.
2. To prepare 100 vials of chymopapain (purified), 125 ml of bulk solution were required. Each vial received 1.0 ml of solution containing 11,500 enzyme units, and 0.02 m moles of sodium cysteinate hydrochloride. The solution was maintained below 10° C. during processing.
3. The bulk solution was prepared as follows:
   a. To about 100 ml of boiled and cooled water for injection was added L-(+) cysteine hydrochloride monohydrate to provide 0.02 m moles per ml in the final volume.
   Mg required = 0.02 m moles/ml × 175.6 mg/m mole × 125 ml
   Mg. added = 439
   After adding the required amount of the solute the pH was adjusted to approximately 5.5 with about 2 ml of 1 N NaOH.
4. Chymopapain was then added to provide 11,500 units per ml in the final volume.

$$\text{Mg required} = \frac{11,500 \text{ units/ml} \times 125 \text{ ml}}{522 \text{ units/ml}}$$

Mg added = 2753.8

The solution was stirred to dissolve all solute, 1 N NaOH was added to bring the pH to 6.0, and sufficient water for injection was added to bring the volume to 125 ml.
5. To sterilize, the solution was passed through a filter of 0.2 micron pore size.
6. To each of 100 5 ml glass vials was then added 1.0 ml of the purified chymopapain-cysteine solution. Split serum vial stoppers were partially inserted, and the vials were inserted into a lyophilizer equipped for automatic stoppering.
7. The vials were retained in the lyophilizer chamber under vaccuum at −30° C. until solidly frozen and the water was removed by gentle heating at a pressure of about 90 microns (absolute) for about 30 hours.
8. The stoppers were then fully seated, the vacuum in the chamber was relieved, and aluminum seals were added.
9. Each vial contained a white, fluffy product which contained 23 mg of chymopapain and 3.5 mg of sodium cysteinate hydrochloride having 11,500 units of enzyme activity.

The following are a series of tests performed to establish the low toxicity and efficacy of the purified chymopapain product.

INTRAVENOUS ACUTE TOXICITY

Acute intravenous toxicity tests were carried out to compare the chymopapain of the prior art purchased commercially in Canada (original source Baxter Travenol Laboratories) (herein called compound A) with the purified chymopapain of the present invention, (herein compound B), and a control, sterile water (compound C) in intravenous injection various test animals. The compound B preparation was prepared by the process of the present invention as an aqueous solution of a lyophilized dosage unit form containing 23.0 milligrams of purified chymopapain and 3.5 milligrams of sodium cysteinate hydrochloride prepared by the method described in the Example above. Compound A contained about 27 mg of crude chymopapain, 0.37 mg. of disodium EDTA, and 3.5 mg of sodium cysteinate hydrochloride.

Test 1 (mice)

Ten young adult mice (five male and five female) of the CD-1 strain were each injected intravenously with 0.01 ml/g (equivalent to 20,000 and 23,000 units/kg of body weight) of the test compounds A and B respectively in solutions having concentrations of 2,000 and 2,300 units/ml. The injection-site chosen was a lateral tail vein and the rate of injection was 1 milliliter per 30 seconds. The mice were observed at $2\frac{1}{2}$ and 4 hours following dosing and twice daily (a.m. and p.m.) thereafter for a total period of 14 days.

Four out of the ten mice treated with compound A died within four hours after receiving the injection. The tails of eight of the surviving mice injected with compound A showed signs of necrosis. Four of the ten mice injected with compound B died at 2 days (one male and one female) and 4 days (two males). One of the surviving mice showed signs of tail necrosis at the end of the test period. No deaths were observed in mice injected with the control (compound C).

Test 2 (rabbits)

Three groups of four rabbits (two male, two female) were injected intravenously with 0.5 ml/kg body weight of the test compounds at dosage levels of 1,000 (compound A) and 1,150 (compound B) units per kg of body weight. Three of four rabbits (two male, one female) died within four hours after injection of Compound A. All of the rabbits injected with compound B survived as did the rabbits injected with the control (compound C).

In summary the tests demonstrated that the prior art chymopapain has a much higher toxicity risk than the purified chymopapain of the present invention.

REDUCED ALLERGENIC PROPERTIES (Guinea Pig Skin Sensitization)

A guinea pig dermal sensitization test was carried out on 32 male adult albino guinea pigs of the Hartley strain maintained in accordance with the Department Health Education and Welfare Pub. No. 78-23 (N.I.H.) for 17 days prior to initiation of the study. The test animals were shaved 26-27 hours prior to testing to remove hair from the flank and back of each guinea pig. Any abnormality of skin (i.e., erythema, lesions) was a basis for rejection from the test as was any deviation in body weight. Thirty test animals were randomly selected from the screen group of 32. Compounds A and B as above-identified were formulated with sterile water to provide injection solutions. The concentration for compound A (commercial chymopapain) was 2,000 units/ml. The concentration for compound B (purified chymopapain) was 2,300 units/ml. A positive control, 2,4-dinitro-1-chlorobenzene was prepared as a 0.1% (W/V) solution identified as Compound D. A negative control (sterile water) was identified as compound C. Ten animals were used in each test group.

Sensitization tests were conducted by inradermal injection of the test compounds A, B and the positive control compound D on the right flank of the animals. Negative control injections (compound C, sterile water) was intradermally injected into the left flank of all test animals in the test groups. The test and controls were injected every other day three times per week until ten sensitizing doses had been administered. The initial volume injected was 0.05 and 0.10 ml on nine subsequent sensitizing doses.

Two weeks after the administration of the tenth sensitizing dose, a challenge dose of 0.05 ml of the test and control compounds were administered in the same manner as the sensitizing doses.

The animals were observed for mortality twice daily (a.m. and p.m.) for 37 days.

The following evaluation of skin lesions were made at 24 and 48 hours after injection and scored for intensity or erythema by measuring diamater (flare) and height of edema (wheal).

The following are the results of the average of the 24 and 48 hour observations.

|  | Diameter of Erythema* | Height of Edema* |
|---|---|---|
| Compound A | 14.8 mm | 2.27 |
| Compound B | 9.9 mm | 1.73 |
| Compound D (positive control) | 11.06 mm | 2.71 |

*average of ten animals except in the case of compound D where two animals died (average of eight)

The results indicate that the commercially available chymopapain formulation has significantly greater sensitization liability than purified chymopapain of the present invention. Compound A had greater sensitization liability than that of positive control (D), 2,4-dinitro-1-chlorobenzene, a known sensitizer. Statistical analysis indicate differences between compounds A and B were significant for erythema ($p \leq 0.025$) and edema $p \leq 0.002$)

DISSOLUTION OF NUCLEUS PULPOSUS (EFFICACY)

The tests compounds A, B and C were each injected into the nucleus pulposus of two consecutive lumbar intervertebral discs of four immature pure bred Beagle dogs at concentrations of (B) 2,300 and 2,000 units/ml of (A) at dosage levels of 115 units (B) and 100 units (A) per disc, respectively. The dogs were examined by spinal radiography, hematology, clinical chemistry, and necroscopy followed by microscopic examination of selected tissues particularly at the injection site.

After 14 days, x-ray films showed narrowing of the intervertebral space in all four dogs injected with compound B, purified chymopapain. In the case of compound A, three of four dogs showed narrowing after 14 days.

At 14 days after injection, four of four animals injected with compound B showed of gross tissue evidence of changes in the discs attributable to treatment whereas only two out of four animal treated with compound A showed these changes. No changes were observed for the control. The animals injected with compound B, purified chymopapin, showed slight to moderate chondroplasia (regrowth of nucleus pulposus) and those injected with compound A showed from very slight to slight changes.

From the foregoing, it is evident that the purified chymopapain prepared by the process of the present invention is a new form of chymopapain which is significantly less toxic than the crude chymopapain of the prior art, particularly as shown in the guinea pig sensitization studies set forth above.

From the experience of other researchers, it is apparent that the new improved purified form of chymopapain of the present invention may be confidently used in the procedure for the treatment of abnormal, damaged, or herniated discs in mammalian subjects including man.

What is claimed is:

1. A pharmaceutical composition consisting of an effective amount of a purified chymopapain product essentially free of proteolytically inactive component materials and characterized by the absence of precipitate formation when a 10% weight/volume solution of said purified chymopapain is acidified with hydrochloric acid followed by treatment with barium chloride; and a minor amount of a pharmaceutically acceptable, non-toxic, reducing agent said composition being further characterized as being free of bisulfite additives.

2. A pharmaceutical composition according to claim 1 wherein the reducing agent is sodium cysteinate hydrochloride.

3. A purified pharmaceutical composition of claim 1 further characterized by being free of ethylene diaminetetraacetic acid.

4. A stable pharmaceutical composition comprising an effective amount of a lyophilized purified chymopapain characterized by being essentially free of proteolytically inactive component materials and bisulfite and relatively non-toxic, and further characterized by the absence of precipitate formation when a 10% weight/volume solution is acidified with hydrochloric acid followed by treatment with barium chloride; and a minor activating amount of a pharmacologically acceptable reducing agent; said reducing agent being present in said composition in an amount of from about 10 to about 20 percent by weight of the purified chymopapain.

5. A pharmaceutical composition according to claim 4 wherein the reducing agent is sodium cysteinate hydrochloride.

6. A composition according to claim 5 wherein the sodium cysteine is present in the amount of at least about 15% by weight of the purified chymopapain solids.

7. A composition according to claim 4 containing about 23 mg of said purified chymopapain.

8. A composition according to claim 7 containing about 3 to 3.6 mg of sodium cysteinate hydrochloride.

9. A stable pharmaceutical composition in dosage unit form for use in dissolving the nucleus pulposus of an intervertebral disc by injection which comprises about 10,000 to about 11,500 proteolytic units of a purified essentially colorless chymopapain, said purified chymopapain being characterized by its being essentially free of protein components which are proteolytically inactive and being free of bisulfite and further characterized by the absence of precipitate when an acidified aqueous solution of said chymopapain is treated with barium chloride reagent and a sodium cysteinate hydrochloride activating agent, said composition being packaged in a vacuum container.

10. A pharmaceutical composition in dosage unit form according to claim 9 wherein the purified chymopapain is present in an amount of 23 milligrams and the sodium cysteinate hydrochloride is present in an amount of about 3.5 milligrams.

11. A method of treating an intervertebral spinal disc in a mammalian subject which disc exhibits an abnormal condition, characterized by a reduced risk of toxic effect to the subject which method comprises the step of injecting into said disc an effective amount of a pharmaceutically acceptable aqueous solution of a purified chymopapain which is essentially free of proteolytically inactive and toxic protein components and bisulfite and is characterized by its failure to form a precipitate in an acidified aqueous solution when treated with a solution of barium chloride, and which solution contains a minor amount of sodium cysteinate hydrochloride solution sufficient to activate the chymopapain, said purified chymopapain being used in amounts sufficient to selectively dissolve the nucleus pulposus of said disc.

12. A method according to claim 11 wherein the abnormal disc is a herniated intervertebral disc.

13. A method according to claim 11 wherein the purified chymopapain is an admixture of chymopapain I and II.

14. A method of treating a herniated intervertebral spinal disc in an mammlian subject which comprises the steps of:
   (a) inserting the needle into said disc;
   (b) confirming the placement of said needle by means of x-ray; and
   (c) injecting into said disc an effective amount of a pharmaceutically acceptable aqueous solution of a relatively non-toxic, purified chymopapain characterized as essentially free of proteolytically inactive components and bisulfite, and by its failure to form a precipitate when an acidified solution thereof is treated with barium chloride reagent, and a pharmaceutically acceptable non-toxic reducing and activating agent for said purified chymopapain; to selectively dissolve said disc.

15. A method according to claim 14 wherein the activating agent is sodium cysteinate hydrochloride.

16. A method according to claim 15 wherein the sodium cysteinate hydrochloride activating agent is present in an amount of at least 10% by weight of the chymopapain on a dry solids basis.

17. A method according to claim 14 wherein the purified chymopapain is an admixture of chymopapain fractions I and II.

* * * * *